(12) United States Patent
Matsui et al.

(10) Patent No.: US 11,219,380 B2
(45) Date of Patent: Jan. 11, 2022

(54) BLOOD PRESSURE PULSE WAVE MEASUREMENT APPARATUS

(71) Applicant: OMRON HEALTHCARE CO., LTD., Muko (JP)

(72) Inventors: Kazuhiro Matsui, Kyoto (JP); Naoki Mori, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 364 days.

(21) Appl. No.: 16/212,563

(22) Filed: Dec. 6, 2018

(65) Prior Publication Data

US 2019/0104952 A1 Apr. 11, 2019

Related U.S. Application Data

(63) Continuation of application No. PCT/JP2017/019564, filed on May 25, 2017.

(30) Foreign Application Priority Data

Jun. 24, 2016 (JP) .............................. JP2016-125859

(51) Int. Cl.
*A61B 5/02* (2006.01)
*A61B 5/022* (2006.01)
(Continued)

(52) U.S. Cl.
CPC ............ *A61B 5/02233* (2013.01); *A61B 5/02* (2013.01); *A61B 5/022* (2013.01);
(Continued)

(58) Field of Classification Search
CPC ............ A61B 5/02108; A61B 5/02233; A61B 5/6824; A61B 5/6829; A61B 5/022;
(Continued)

(56) References Cited

U.S. PATENT DOCUMENTS 4,779,626 A 10/1988 Peel et al.
5,730,139 A * 3/1998 Miyazaki ............. A61B 5/0225
600/493

(Continued)

FOREIGN PATENT DOCUMENTS

JP S63-068133 A 3/1988
JP 2000-316821 A 11/2000
(Continued)

OTHER PUBLICATIONS

Aug. 8, 2017 International Search Report issued in International Patent Application No. PCT/JP2017/019564.

Primary Examiner — Christian Jang
Assistant Examiner — Anna Roberts
(74) Attorney, Agent, or Firm — Oliff PLC (57) ABSTRACT

A blood pressure pulse wave measurement apparatus includes: first and second cuffs for pressing upper and lower limbs of a measurement subject; first and second detection units configured to detect first and second pulse waves transmitted from the cuffs through first and second tubes; and a control unit configured to calculate an ankle-brachial blood pressure ratio and a pulse wave velocity using the pulse waves. First and second delay elements are provided at specific positions in the lengthwise directions of the tubes. The first delay element delays a transfer characteristic of the first tube so the transfer characteristic of the first tube matches a transfer characteristic of a tube having a predetermined first reference length, and the second delay element delays a transfer characteristic of the second tube so the transfer characteristic of the second tube matches a transfer characteristic of a tube having a predetermined second reference length.

3 Claims, 8 Drawing Sheets

(51) Int. Cl.
  *A61B 5/021* (2006.01)
  *A61B 5/00* (2006.01)
(52) U.S. Cl.
  CPC ........ *A61B 5/02108* (2013.01); *A61B 5/6824* (2013.01); *A61B 5/6829* (2013.01)
(58) Field of Classification Search
  CPC ............ A61B 5/02116; A61B 5/02125; A61B 5/02241; A61B 5/02208; A61B 5/02225; A61B 5/6825; A61B 5/6826; A61B 5/6828
  See application file for complete search history.

(56) References Cited

U.S. PATENT DOCUMENTS

| | | | |
|---|---|---|---|
| 2004/0039290 A1 | 2/2004 | Narimatsu et al. | |
| 2011/0152700 A1* | 6/2011 | Sawanoi | A61B 5/7221 600/493 |
| 2011/0282221 A1* | 11/2011 | Sawanoi | A61B 5/02141 600/493 |
| 2012/0095353 A1* | 4/2012 | Mori | A61B 5/7242 600/500 |
| 2014/0163402 A1* | 6/2014 | Lamego | A61B 5/0235 600/493 |
| 2014/0243691 A1* | 8/2014 | Osaki | A61B 5/02108 600/490 |
| 2014/0316291 A1* | 10/2014 | Osaki | A61B 5/742 600/492 |

FOREIGN PATENT DOCUMENTS

| | | | |
|---|---|---|---|
| JP | 2003-290160 A | | 10/2003 |
| JP | 2004-073721 A | | 3/2004 |
| JP | 2004-073722 A | | 3/2004 |
| JP | 2004073722 A | * | 3/2004 |
| JP | 2007-037648 A | | 2/2007 |
| JP | 2016-052605 A | | 4/2016 |

* cited by examiner

BLOOD PRESSURE PULSE WAVE MEASUREMENT APPARATUS

This is a Continuation of International Application No. PCT/JP2017/019564 filed May 25, 2017, which claims the benefit of Japanese Application No. 2016-125859 filed Jun. 24, 2016. The disclosure of the prior applications is hereby incorporated by reference herein in its entirety.

TECHNICAL FIELD

The present invention relates to a blood pressure pulse wave measurement apparatus.

BACKGROUND ART

Conventionally, the ankle brachial index (ABI) has been widely used in diagnosis of arteriosclerosis as an index indicating clogging of blood vessels, and the pulse wave velocity (PWV) has been widely used in diagnosis of arteriosclerosis as an index indicating hardness of blood vessels.

Although the ABI and PWV are indices that are used individually, if arteriosclerosis has spread over the entire body, for example, values in a normal range are sometimes obtained through measurement of only the ABI, and if the value of the ABI is normal, it is understood that keeping track of the progress of arteriosclerosis in the entire body using the PWV will aid more accurate diagnosis.

For this reason, in order to facilitate this kind of multi-faceted diagnosis, a measurement apparatus obtained by integrating in an ABI measurement apparatus and a PWV measurement apparatus, which are conventionally separate apparatuses, has appeared on the market in recent years.

Conventionally, as disclosed in Patent Document 1 (JP 2000-316821A) for example, a device in which four cuffs for the upper arms and ankles are connected to a main body and the cuffs are connected to the arms and legs of a measurement subject to perform measurement has been known as this kind of blood pressure pulse wave measurement apparatus. A detection means for detecting pulse waves from the cuffs for the upper arms and the ankles is included in the main body. Here, in order to attach the cuffs for the upper arms and the ankles to the upper arms and ankles of the measurement subject, tubes extending from the main body need to be extended and attached to the upper arms and ankles of the measurement subject, and the multiple tubes get tangled with each other, requiring a large amount of labor and time.

CITATION LIST

Patent Literature

Patent Document 1: JP 2000-316821A

SUMMARY OF INVENTION

Technical Problem

Under this circumstance, the applicants of the present invention previously proposed a blood pressure pulse wave measurement apparatus constituted by a first housing that is connected to an upper arm cuff and includes a detection means for detecting a pulse wave from the upper arm cuff, and a second housing that is connected to an ankle cuff and includes a detection means for detecting a pulse wave from the ankle cuff (JP 2016-052605A). With this blood pressure pulse wave measurement apparatus, the inconvenience of the tubes becoming tangled can be avoided. For example, the length of the tube connecting the upper arm cuff and the first housing is set to 2 meters, and the length of the tube connecting the ankle cuff and the second housing is set to 50 centimeters. A measurement algorithm for the ABI and PWV is defined with the lengths of these tubes as reference lengths.

Here, if the length of the tube connecting the upper arm cuff and the first housing and the length of the tube connecting the ankle cuff and the second housing are changed, the time needed for the pulse wave to be transmitted through the tube changes, and therefore the above-described measurement algorithm for the ABI and PWV also needs to be changed. For this reason, a change in design requires a large amount of labor and time.

In view of this, the present invention aims to provide a blood pressure pulse wave measurement apparatus in which the length of the tube connecting the upper arm cuff and the first housing and the length of the tube connecting the lower limb cuff and the second housing can be changed without changing the measurement algorithm for the ABI and PWV.

Solution to the Problem

In order to solve the above-described problem, a blood pressure pulse wave measurement apparatus of the present invention is a blood pressure pulse wave measurement apparatus for measuring an ankle brachial index and a pulse wave velocity, including:

a first cuff for pressing an upper limb of a measurement subject;

a second cuff for pressing a lower limb of the measurement subject;

a first detection unit that is connected to the first cuff via a first tube and is configured to detect a first pulse wave transmitted from the first cuff through the first tube in a lengthwise direction of the tube;

a second detection unit that is connected to the second cuff via a second tube and is configured to detect a second pulse wave transmitted from the second cuff through the second tube in a lengthwise direction of the tube; and a control unit configured to respectively calculate an ankle-brachial blood pressure ratio and a pulse wave velocity using the first and second pulse waves, wherein first and second delay elements are respectively provided at specific positions in the lengthwise directions of the first tube and the second tube, the first delay element delays a transfer characteristic of the first tube such that the transfer characteristic of the first tube matches a transfer characteristic of a tube having a predetermined first reference length, and the second delay element delays a transfer characteristic of the second tube such that the transfer characteristic of the second tube matches a transfer characteristic of a tube having a predetermined second reference length.

In the present specification, the pulse wave velocity typically indicates the brachial-ankle pulse wave velocity (baPWV) and the heart-ankle pulse wave velocity (haPWV). Note that the cardio-ankle vascular index (CAVI), which is an index reflecting the hardness of the arteries from the heart to the ankle, can be calculated by correcting the heart-ankle pulse wave velocity haPWV using a logarithmic pulse wave. Also, the ankle brachial index typically indicates the ankle brachial pressure index ABI.

With the blood pressure pulse wave measurement apparatus of the present invention, a first delay element is provided at a specific position in the lengthwise direction of the first tube connecting the first cuff and the first detection unit. Also, a second delay element is provided at a specific position in the lengthwise direction of the second tube connecting the second cuff and the second detection unit. Here, the first delay element delays the transfer characteristic of the first tube such that the transfer characteristic of the first tube matches a transfer characteristic of a tube having a predetermined first reference length, and the second delay element delays the transfer characteristic of the second tube such that the transfer characteristic of the second tube matches a transfer characteristic of a tube having a predetermined second reference length. With this configuration, the length of the tube connecting the upper limb cuff and the first housing and the length of the tube connecting the lower limb cuff and the second housing can be changed without needing to change the measurement algorithm for the ABI and PWV, which were defined for tubes having the first reference length and the second reference length.

With a blood pressure pulse wave measurement apparatus of an embodiment, the first detection unit is arranged in a first housing and the second detection unit is arranged in a second housing, the first delay element is provided on an end portion of the first tube in the first housing, and the second delay element is provided on an end portion of the second tube in the second housing.

With the blood pressure pulse wave measurement apparatus of this embodiment, the first delay element is provided in the first housing and the second delay element is provided in the second housing, and therefore they do not become hindrances when the measurement subject attaches the upper arm and ankle cuffs to the upper arm and ankle of the measurement subject.

With a blood pressure pulse wave measurement apparatus of an embodiment, the first delay element and the second delay element are air tanks storing air of a predetermined capacity.

With the blood pressure pulse wave measurement apparatus of this embodiment, the blood pressure pulse wave measurement apparatus can be attached easily to an existing product and can easily be made smaller.

Advantageous Effects of the Invention

As is clear from the description above, with the blood pressure pulse wave measurement apparatus of the present invention, the lengths of the tubes connected to the upper limb cuff and the lower limb cuff can be changed easily without needing to change the measurement algorithm for the ABI and PWV, which are defined for tubes having a first reference length and a second reference length.

DESCRIPTION OF EMBODIMENTS

Hereinafter, embodiments of the present invention will be described with reference to the drawings. Note that in the following embodiments, similar constituent elements are denoted by the same reference numerals and redundant description thereof is omitted.

EMBODIMENT

Figure 1:
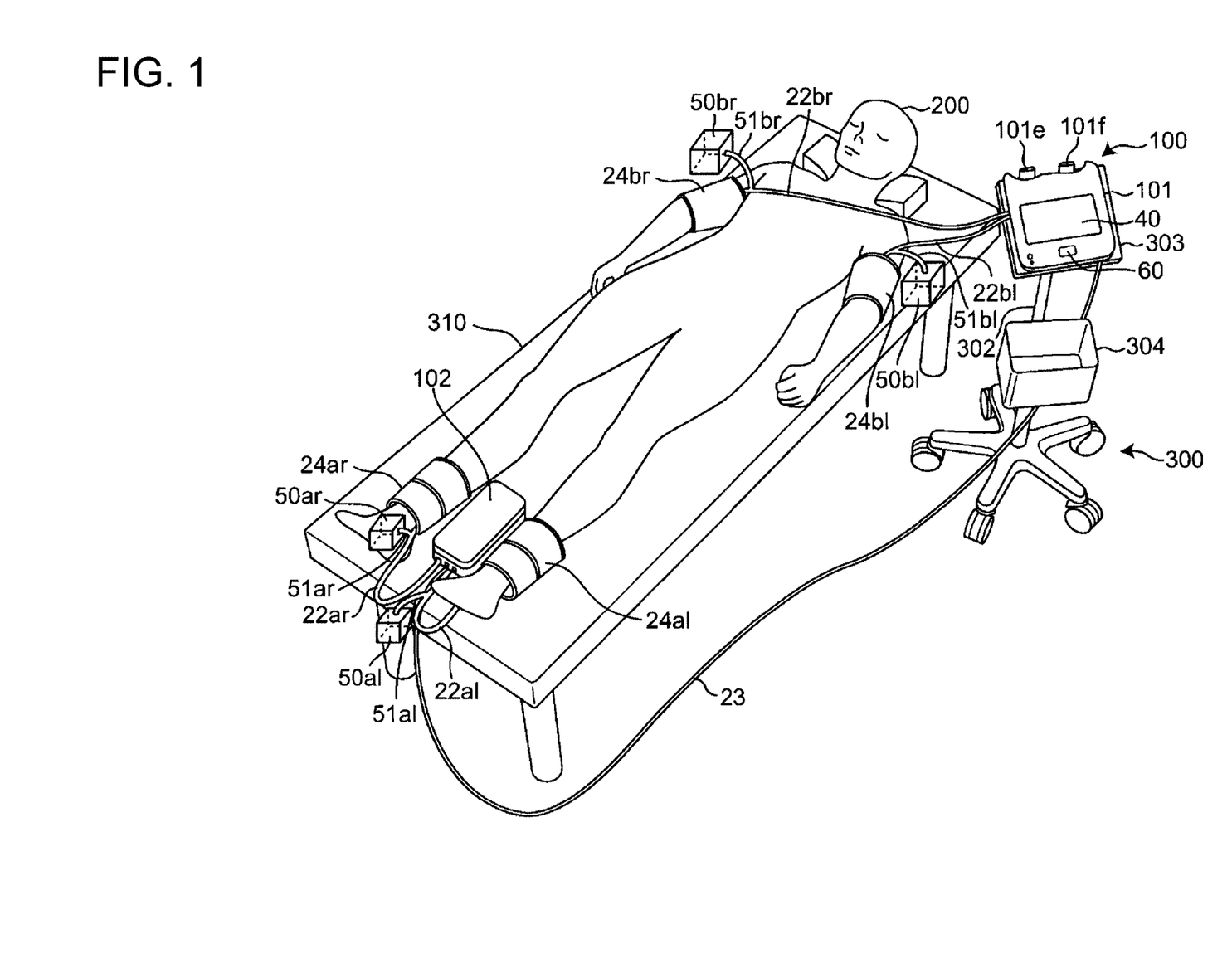
FIG. 1 is a perspective view showing a state in which a blood pressure pulse wave measurement apparatus 100 according to an embodiment of the present invention is used.

FIG. 1 is a perspective view showing a state in which a blood pressure pulse wave measurement apparatus of the present invention is used. The blood pressure pulse wave measurement apparatus 100 includes a main unit 101, which is a first housing, an ankle unit 102, which is a second housing, and four cuffs 24ar, 24al, 24br, and 24bl.

As shown in FIG. 1, a storage wagon 300 includes legs 301 with casters, a support column 302 provided in a standing manner on the legs 301, a placement platform 303 attached to the leading end of the support column 302, and a storage box 304 that is attached to the support column 302 and has an opening facing upward. The main unit 101 is placed on the placement platform 303. The ankle unit 102, right ankle (right lower limb) and left ankle (left lower limb) cuffs 24ar and 24al serving as second cuffs are stored in the storage box 304. The right upper arm (right upper limb) and left upper arm (left upper limb) cuffs 24br and 24bl serving as first cuffs are held by being hung on hooks 101e and 101f provided on the rear portion of the main unit 101.

The main unit 101 and the right upper arm (right upper limb) and left upper arm (left upper limb) cuffs 24br and 24bl are connected by tubes 22br and 22bl serving as first tubes through which air for increasing the cuff pressure is to be passed. Furthermore, air tanks 50br and 50bl serving as first delay elements for storing air of a predetermined first capacity are respectively connected via tubes 51br and 51bl at specific positions in the lengthwise directions of the tubes 22br and 22bl. Here, the length of the tube 22br and the length of the tube 22bl are approximately the same, and the length of the tube 51br and the length of the tube 51bl are approximately the same. Here, the air tanks 50br and 50bl are respectively provided as delay elements at any position of the tubes 22br and 22bl such that the fluid transfer characteristics of the tubes 22br and 22bl connecting the main unit 101 and the cuffs 24br and 24bl match the fluid transfer characteristic of a tube having a predetermined first reference length. In this example, the first reference length is set to 2 meters.

Similarly, the ankle unit 102 and the right ankle (right lower limb) and left ankle (left lower limb) cuffs 24ar and 24al are connected by tubes 22ar and 22al serving as second tubes through which air for increasing the cuff pressure is to be passed. Furthermore, air tanks 50ar and 50al serving as second delay elements for storing air of a predetermined second capacity are respectively connected via tubes 51ar and 51al at specific positions in the lengthwise directions of the tubes 22ar and 22al. Here, the length of the tube 22ar and the length of the tube 22al are approximately the same, and the length of the tube 51ar and the length of the tube 51al are approximately the same. Here, the air tanks 50ar and 50al are respectively provided as delay elements at any position of the tubes 22ar and 22al such that the fluid transfer characteristics of the tubes 22ar and 22al connecting the ankle unit 102 and the cuffs 24ar and 24al match the fluid transfer characteristic of a tube having a predetermined second reference length. In this example, the second reference length is set to 50 centimeters.

Also, the main unit 101 is connected to the ankle unit 102 by a connection cable 23 so as to be able to supply power thereto and communicate therewith.

As shown in FIG. 1, a measurement subject 200 lies facing upward on a bed 310. The ankle unit 102 is taken out of the storage box 304 and is placed on the bed 310 between the right ankle and left ankle of the measurement subject 200.

The cuffs 24ar, 24al, 24br, and 24bl are attached to the respective limbs of the measurement subject. Specifically, they are respectively attached to the right ankle (right lower limb), left ankle (left lower limb), right upper arm (right upper limb), and left upper arm (left upper limb).

Note that in the following description, only an example in which the cuffs are attached to the right ankle, left ankle, right upper arm, and left upper arm will be described. However, "limb" indicates a part included in the arms and legs, and thus may be a hand, a fingertip, or the like. The cuffs 24ar, 24al, 24br, and 24bl will be collectively referred to as "cuffs 24" unless it is necessary to make a distinction therebetween.

Figure 2:
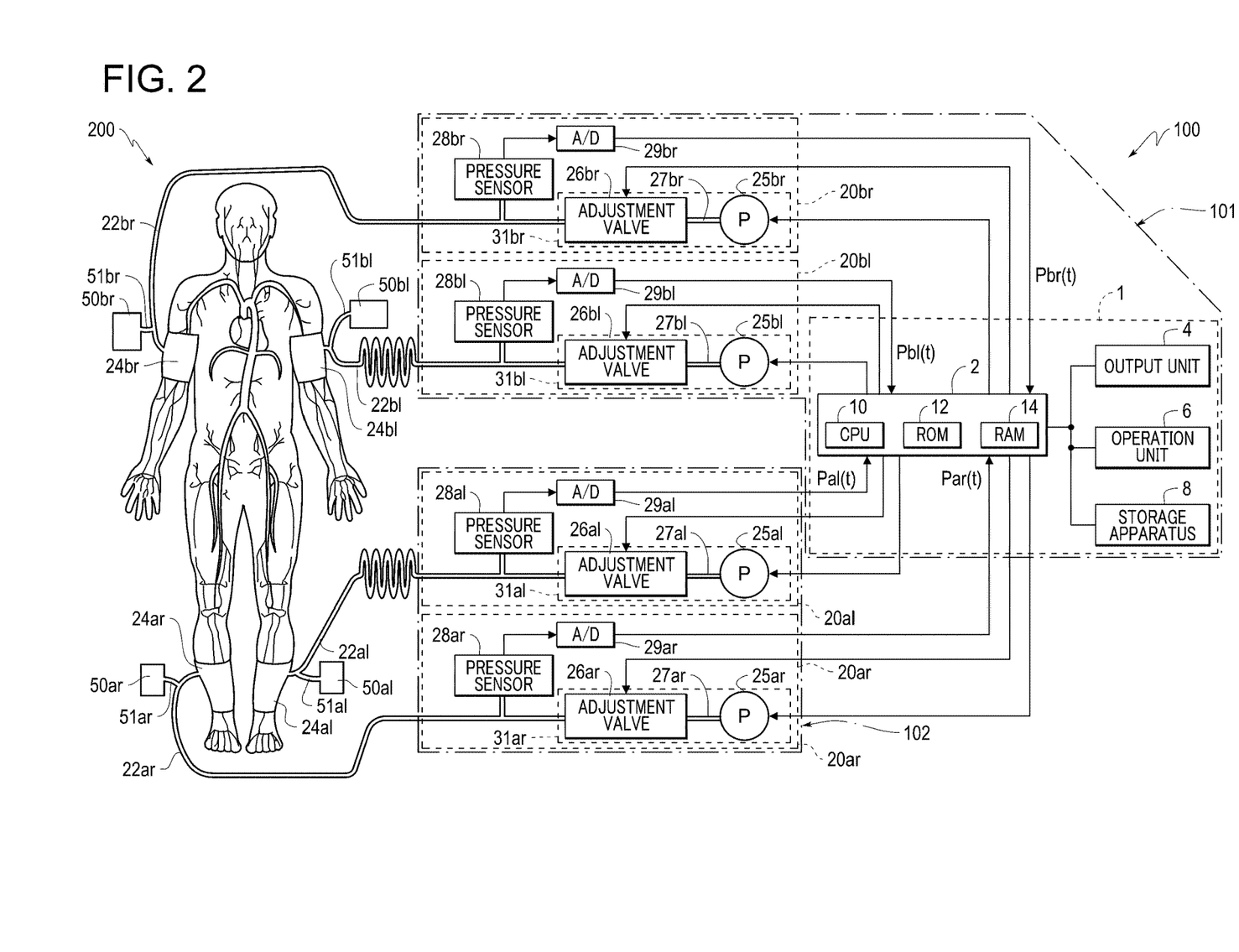
FIG. 2 is a block diagram schematically showing a configuration of a control system inside of the blood pressure pulse wave measurement apparatus 100 shown in FIG. 1.

FIG. 2 is a block diagram schematically showing a control system inside of the blood pressure pulse wave measurement apparatus 100 shown in FIG. 1. As shown in FIG. 2, the ankle unit 102 includes two detection units 20ar and 20al serving as second detection units. The main unit 101 includes an information processing unit 101 and two detection units 20br and 20bl serving as first detection units.

The detection units 20ar, 20al, 20br, and 20bl include hardware that is needed to detect pulse waves of the limbs of the measurement subject 200. The configurations of the detection units 20ar, 20al, 20br, and 20bl may all be similar, and therefore the detection units 20ar, 20al, 20br, and 20bl will be collectively referred to as "detection units 20" unless it is necessary to make a distinction therebetween.

The information processing unit 1 includes a control unit 2, an output unit 4, an operation unit 6, and a storage apparatus 8.

The control unit 2 is an apparatus that performs overall control of the blood pressure pulse wave measurement apparatus 100, and is representationally constituted by a computer including a CPU (Central Processing Unit) 10, a ROM (Read Only Memory) 12, and a RAM (Random Access Memory) 14.

The CPU 10 corresponds to an arithmetic processing unit, reads out programs stored in advance in the ROM 12, and executes the programs while using the RAM 14 as a work memory.

Also, the output unit 4, the operation unit 6, and the storage apparatus 8 are connected to the control unit 2. The output unit 4 outputs the measured pulse wave, pulse wave analysis results, and the like. The output unit 4 may be a display device constituted by an LED (Light Emitting Diode) or an LCD (Liquid Crystal Display), or the like, or may be a printer (driver). In this example, as shown in FIG. 1, a display screen 40 of an LCD is provided as the output unit 4.

The operation unit 6 shown in FIG. 2 receives an instruction from the user. In this example, as shown in FIG. 1, an operation switch 60 is provided as the operation unit 6 on the upper surface of the main unit 101. The user can input an instruction such as turning on or off the power, or starting blood pressure measurement using the operation switch 60.

The storage apparatus 8 shown in FIG. 2 stores various types of data and programs. The CPU 10 of the control unit 2 performs reading out and writing of data and programs stored in the storage apparatus 8. The storage apparatus 8 may be constituted by a hard disk, a non-volatile memory (e.g., a flash memory), a detachable external storage medium, or the like, for example.

Next, the configuration of the detection units 20 will be described specifically.

The detection unit 20br is a detection unit that is connected to the cuff 24br via the tube 22br and detects a pulse wave transmitted through the tube 22br. Specifically, the detection unit 20br detects the pulse wave of the right upper arm by performing adjustment and detection of the internal pressure of the cuff 24br (hereinafter referred to as "cuff pressure") attached to the right upper arm of the measurement subject 200. The cuff 24br contains a fluid bladder (not shown) (in this example, an air bladder).

The detection unit 20br includes a pressure sensor 28br, a cuff drive unit 31br, and an A/D (Analog to Digital) conversion unit 29br. The cuff drive unit 31br sends air into the cuff 24br via the tube 22br and increases the pressure of the cuff 24br. Also, the cuff drive unit 31br includes an adjustment valve 26br, a pressure pump 25br, and a tube 27br that connects the adjustment valve 26br and the pressure pump 25br. The cuff 24br, the pressure sensor 28br, and the adjustment valve 26br are connected by the tube 22br. Here, the air tank 50br is connected to the end portion of the tube 22br on the cuff 24br side via the tube 51br.

The pressure sensor 28br is a detection part for detecting pressure fluctuations transmitted via the tube 22br, and for example, includes multiple sensor elements aligned at a predetermined interval in a semiconductor chip composed of single-crystal silicon or the like. The pressure fluctuation signal detected by the pressure sensor 28br is converted into a digital signal by the A/D conversion unit 29br and is input to the control unit 2 as a pulse wave signal pbr(t).

The adjustment valve 26br is inserted between the pressure pump 25br and the cuff 24br and keeps the pressure used to increase the pressure of the cuff 24br in a predetermined range during measurement. The pressure pump 25br operates according to a detection command from the control unit 2 and supplies air to the fluid bladder (not shown) in the cuff 24br in order to increase the pressure of the cuff 24br.

Due to this pressure increase, the cuff 24br presses a measurement site and the pressure changes corresponding to the pulse wave of the right upper arm are transmitted to the detection unit 20br via the tube 22br. The detection unit 20br detects the pulse wave of the right upper arm by detecting the transmitted pressure changes.

The detection unit 20bl also similarly includes a pressure sensor 28bl, a cuff drive unit 31bl, an adjustment valve 26bl, a pressure pump 25bl, and an A/D conversion unit 29bl. The cuff drive unit 31bl sends air into the cuff 24bl via the tube 22bl, and increases the pressure of the cuff 24bl. Also, the cuff drive unit 31bl includes the adjustment valve 26bl, the pressure pump 25bl, and a tube 27bl that connects the adjustment valve 26bl and the pressure pump 25bl. The cuff 24bl, the pressure sensor 28bl, and the adjustment valve 26bl are connected by the tube 22bl. Here, the air tank 50bl is connected to the end portion of the tube 22bl on the cuff 24bl side via the tube 51bl. The pressure sensors 28br and 28bl respectively detect the pulse waves (first pulse waves) transmitted through the tubes 22br and 22bl.

Also, the detection unit 20ar includes a pressure sensor 28ar, a cuff drive unit 31ar, an adjustment valve 26ar, a pressure pump 25ar, and an A/D conversion unit 29ar. The cuff drive unit 31ar sends air into the cuff 24ar via the tube 22ar and increases the pressure of the cuff 24ar. Also, the cuff drive unit 31ar includes the adjustment valve 26ar, the pressure pump 25ar, and a tube 27ar that connects the adjustment valve 26ar and the pressure pump 25ar. The cuff 24ar, the pressure sensor 28ar, and the adjustment valve 26ar are connected by the tube 22ar. Here, the air tank 50ar is connected to the end portion of the tube 22ar on the cuff 24ar side via the tube 51ar.

The detection unit 20al also similarly includes a pressure sensor 28al, a cuff drive unit 31al, an adjustment valve 26al, a pressure pump 25al, and an A/D conversion unit 29al. The cuff drive unit 31al sends air into the cuff 24al via the tube 22al, and increases the pressure of the cuff 24al. Also, the cuff drive unit 31al includes the adjustment valve 26al, the pressure pump 25al, and a tube 27al that connects the adjustment valve 26al and the pressure pump 25al. The cuff 24al, the pressure sensor 28al, and the adjustment valve 26al are connected by the tube 22al. Here, the air tank 50al is connected to the end portion of the tube 22al on the cuff 24al side via the tube 51al. The pressure sensors 28ar and 28al respectively detect the pulse waves (second pulse waves) transmitted through the tubes 22ar and 22al.

Since the functions of the units in the detection units 20bl, 20ar, and 20al are similar to those of the detection unit 20br, detailed description will not be repeated here. Also, the units in the detection units 20 will be described with the signs "ar", "br", and the like omitted unless it is necessary to make a distinction therebetween.

Through the control performed by the control unit 2 (in particular, the CPU 10), the blood pressure pulse wave measurement apparatus 100 performs blood pressure measurement using a known oscillometric method as shown in the processing flow shown in FIG. 3A, which will be described later. Also, the blood pressure pulse wave measurement apparatus 100 performs pulse wave detection to obtain the brachial-ankle pulse wave velocity baPWV and the heart-ankle pulse wave velocity haPWV as the pulse wave velocities, and to obtain the ankle brachial pressure index ABI as the ankle brachial index. That is, the control unit 2 calculates the ankle brachial pressure index (ABI) and the pulse wave velocity (PWV) using the pulse waves detected by the detection units 20br, 20bl, 20al, and 20ar. As is known, the brachial-ankle pulse wave velocity baPWV is an index indicating the hardness of blood vessels, and the ankle brachial pressure index ABI is an index indicating clogging of blood vessels.

Operations of the blood pressure pulse wave measurement apparatus 100 configured as described above will be described below.

Figure 3A:
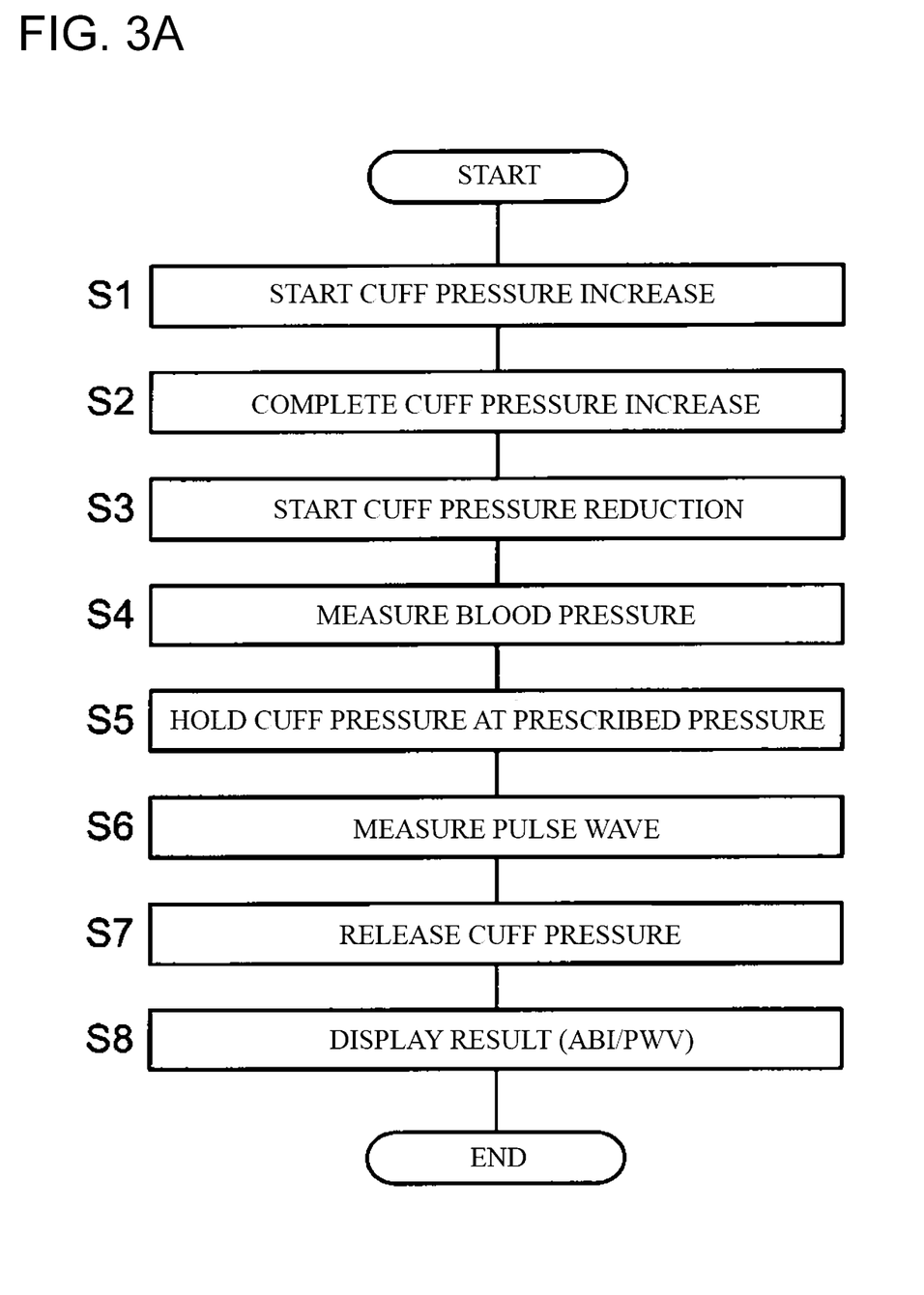
FIG. 3A is a flowchart showing ankle brachial index and pulse wave velocity measurement processing executed by the blood pressure pulse wave measurement apparatus shown in FIG. 1.
Figure 3B:
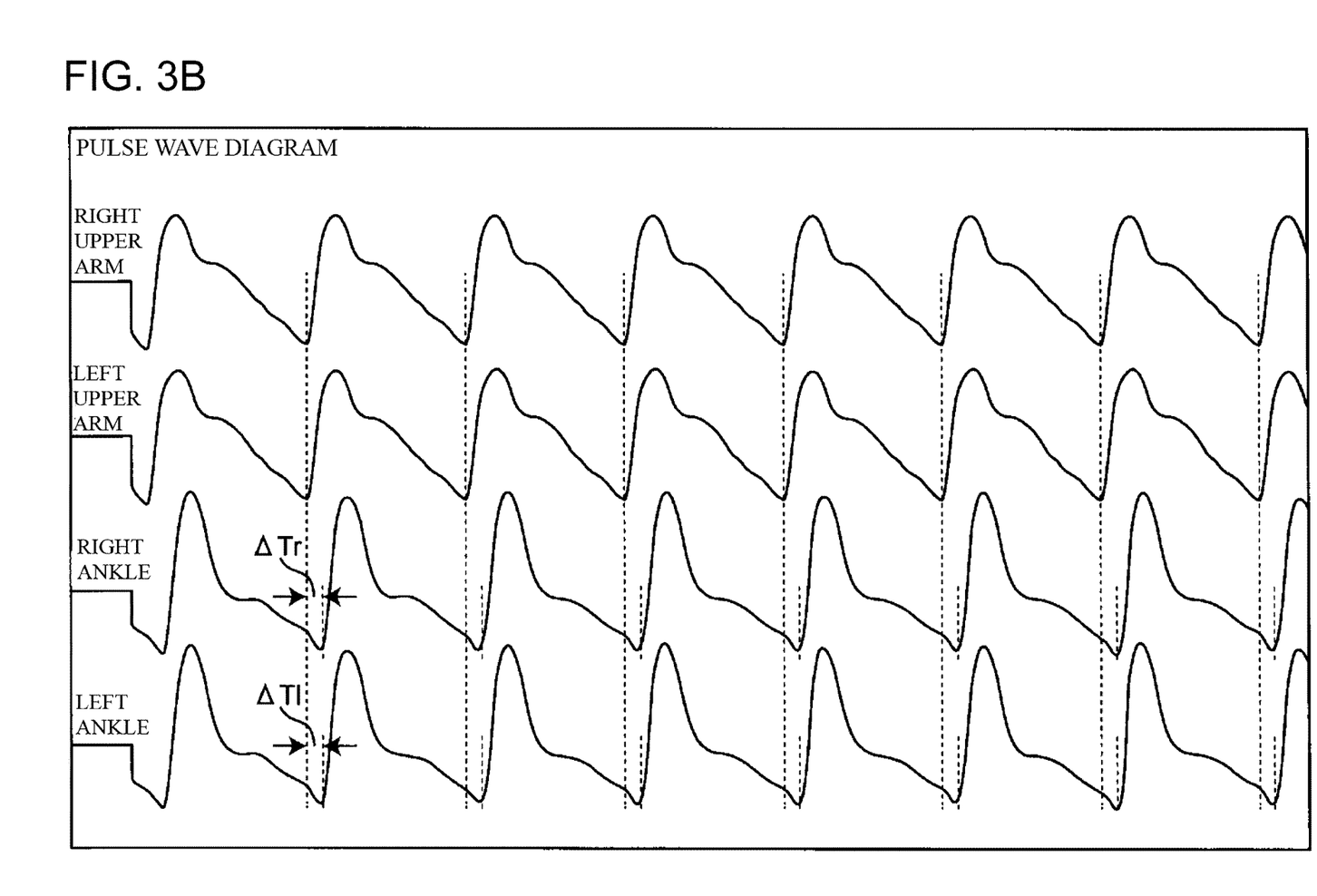
FIG. 3B is a diagram showing pulse wave waveforms detected by a pressure sensor of the blood pressure pulse wave measurement apparatus 100 shown in FIG. 1.

FIG. 3A is a flowchart showing ankle brachial index and pulse wave velocity measurement processing executed by the blood pressure pulse wave measurement apparatus 100, and FIG. 3B is a diagram showing a pulse wave waveform detected by the pressure sensor of the blood pressure pulse wave measurement apparatus 100 shown in FIG. 1. Specifically, when measurement is started, as shown in step S1 in FIG. 3A, the pumps 25 in the detection units 20 are driven and the pressure increase of the cuffs 24 is started.

Then, as shown in step S2, the cuff pressure is increased to a predetermined pressure (a pressure higher than the systolic blood pressure of the measurement subject 200) while the cuff pressure is monitored by the pressure sensor 28, and the pumps 25 are stopped (complete cuff pressure increase). Next, as shown in step S3, the adjustment valve 26 is controlled, pressure reduction of the cuffs 24 is started, and the cuff pressure is gradually reduced. In this pressure reduction process, fluctuations in the artery volume that occur in the arteries of the measurement sites are detected as pulse wave signals by the pressure sensor 28 via the cuffs 24.

Then, as shown in step S4, the systolic blood pressure and diastolic blood pressure are calculated by applying a predetermined algorithm for a known oscillometric method, based on the amplitudes of the pulse wave signals (measure blood pressure). Along with this, the CPU 10 functions as an ankle brachial index acquisition unit to calculate the ankle brachial pressure indices ABI=(ankle systolic blood pressure)/(brachial systolic blood pressure) for the left half and right half of the body of the measurement subject 200. Also, in this example, the pulse (units: beats per minute) is also calculated. Note that calculation of the blood pressure is not limited to the pressure reduction process and may be performed in the pressure increase process.

Next, as shown in step S5, the adjustment valve 26 is closed and the cuff pressure is held at a prescribed pressure (e.g., about 50 mmHg). In this state, as shown in step S6, the CPU 10 functions as the pulse wave transmission velocity acquisition unit and measures the pulse wave using the pressure sensor 28. At this time, a pulse wave waveform such as that shown in FIG. 3B is obtained, for example. In this example, a delay in the rising edge of the waveform for the left ankle with respect to the rising edge of the waveform for the right upper arm of the measurement subject 200 is $\Delta Tl$. Also, the delay in the rising edge of the waveform for the right ankle with respect to the rising edge of the waveform for the right upper arm of the measurement subject 200 is $\Delta Tr$. The brachial-ankle pulse wave velocity baPWV is calculated for the right upper arm-left upper arm and the right upper arm-right ankle of the measurement subject 200 according to the following equation based on the delays $\Delta Tl$ and $\Delta Tr$.

$$baPWV=(La-Lb)/\Delta T$$

Here, La indicates the distance from the aortal root to the ankle, and Lb indicates the distance from the aortal root to the upper arm. ΔT indicates ΔTl or ΔTr (for the sake of simplicity, the signs "l" and "r" are omitted). The brachial-ankle pulse wave velocities baPWV calculated using ΔTl and ΔTr are called the brachial-ankle pulse wave velocity baPWV for the left half of the body and the brachial-ankle pulse wave velocity baPWV for the right half of the body.

When the measurement is complete, as shown in step S7 in FIG. 3A, the adjustment valve 26 is fully opened and the cuff pressure is released. Then, as shown in step S8, the CPU 10 functions as a display processing unit to display the measurement results on the display screen 40 (see FIG. 1) provided on the upper surface of the main unit 101.

WORKING EXAMPLES

Working Example 1

Figure 4A:
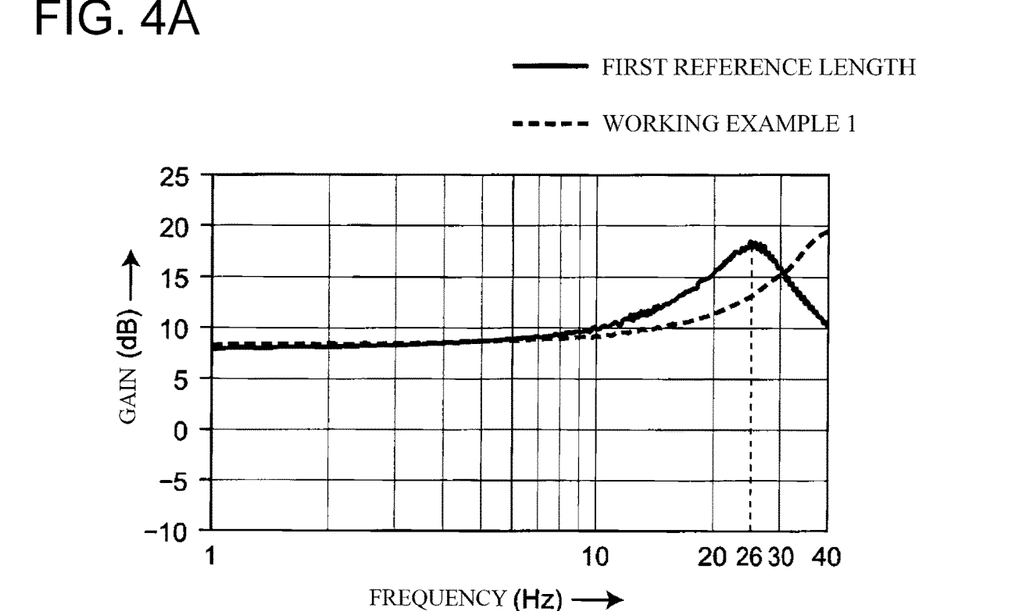
FIG. 4A is a graph relating to a fluid transfer characteristic, indicating a change in gain with respect to a frequency of a tube 22br shown in FIG. 1, when a capacity of an air tank 50br shown in FIG. 1 is set to 0 cc.
Figure 4B:
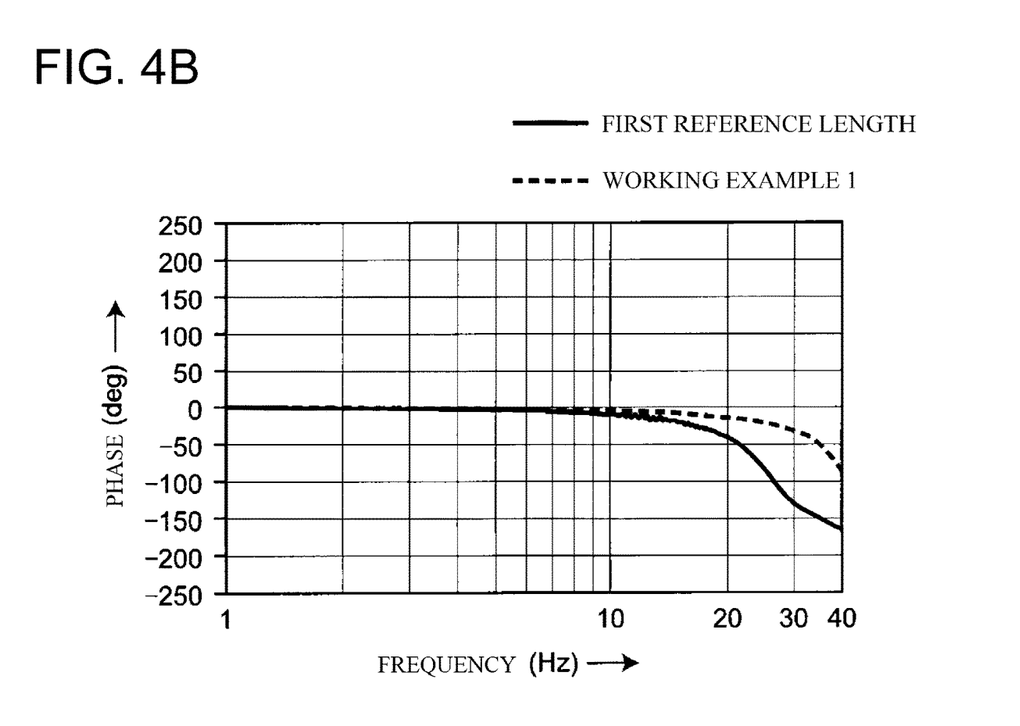
FIG. 4B is a graph relating to a fluid transfer characteristic, indicating a change in phase with respect to the frequency of the tube 22br shown in FIG. 1, when the capacity of the air tank 50br shown in FIG. 1 is set to 0 cc.

First, changes in the fluid transfer characteristic of the tube 22br when the length of the tube 22br is 1.1 meters, which is contracted compared to 2 meters, which is the first reference length, will be described below.

FIG. 4A is a graph relating to the fluid transfer characteristic, indicating the change in the gain with respect to the frequency of the tube 22br shown in FIG. 1, when the capacity of the air tank 50br shown in FIG. 1 is set to 0 cc, and FIG. 4B is a graph relating to the fluid transfer characteristic, indicating the change in the phase with respect to the frequency of the tube 22br shown in FIG. 1, when the capacity of the air tank 50br shown in FIG. 1 is set to 0 cc. In FIGS. 4A and 4B, the fluid transfer characteristic of the tube 22br when the length of the tube 22br is set to 2 meters (reference length) is indicated by a solid line, and the fluid transfer characteristic of the tube 22br when the length of the tube 22br is set to 1.1 meters is indicated by a dotted line. As shown in FIG. 4A, it is understood that the peak of the gain that occurs when the frequency is 26 (Hz) is shifted to a frequency of 40 (Hz). Also, as shown in FIG. 4B, it is understood that shifting has occurred in the curve indicating the change in the phase when the length of the tube 22br is set to 2 meters (reference length) and the curve indicating the change in the phase when the length of the tube 22br is set to 1.1 meters.

That is, as shown in FIGS. 4A and 4B, it is understood that shifting occurs in the fluid transfer characteristic of the tube 22br due to the length of the tube 22br being changed from the reference length. Note that the same applies to the tubes 22bl, 22ar, and 22al.

Here, in the present invention, the above-described shifting is corrected by providing the air tanks having the predetermined capacity in the tubes 22br, 22bl, 22ar, and 22al. With this configuration, no error occurs in the data measured using the tube 22br with the changed length, even if the ABI and PWV are measured using a measurement algorithm defined for the tube 22br having the reference length. Note that the same applies to the tubes 22bl, 22ar, and 22al.

Figure 5:
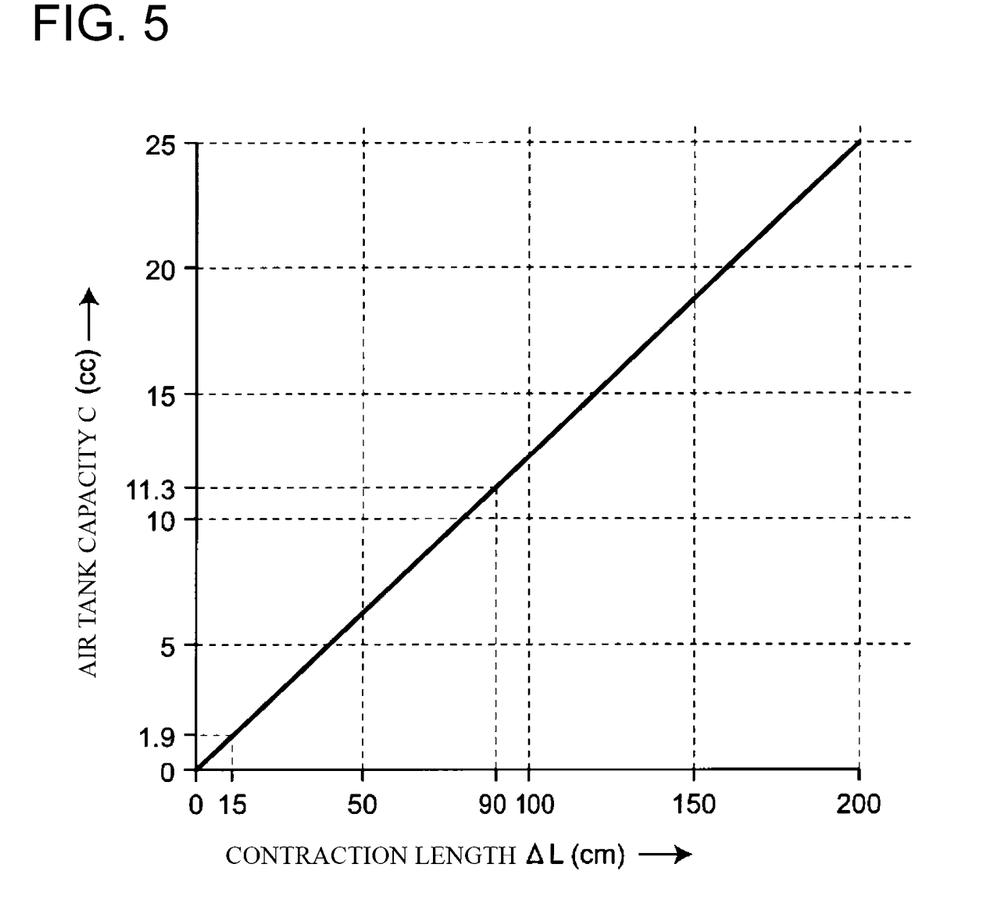
FIG. 5 is a graph showing a relationship between a contraction length ΔL (cm) of the tube 22br shown in FIG. 1 and an air tank capacity (cc) that is needed in order to correct shifting (shifting described in FIGS. 4A and 4B) caused by the contraction length ΔL (cm).

Next, a method for setting the capacity of the air tank 50br provided in the tube 22br will be described below.

FIG. 5 is a graph showing a relationship between a contraction length ΔL (cm) of the tube 22br shown in FIG. 1 and the air tank capacity (cc) that is needed to correct the shifting (the shifting illustrated in FIGS. 4A and 4B) occurring due to the contraction length ΔL (cm). Here, the contraction length ΔL refers to the length by which the length of the tube 22br is reduced from the reference length.

FIG. 5 shows the capacity of the air tank that is needed to correct the shifting illustrated in FIGS. 4A and 4B. In the present embodiment, the contraction length ΔL of the tube 22br is 90 (centimeters) (=2 (meters)−1.1 (meters)). Accordingly, with reference to FIG. 5, the capacity of the air tank 50br is set to 11.3 (cc). Hereinafter, the effect in the case of setting the capacity of the air tank 50br to 11.3 (cc) will be described. Note that the same applies to the air tank 50bl as well.

Figure 6A:
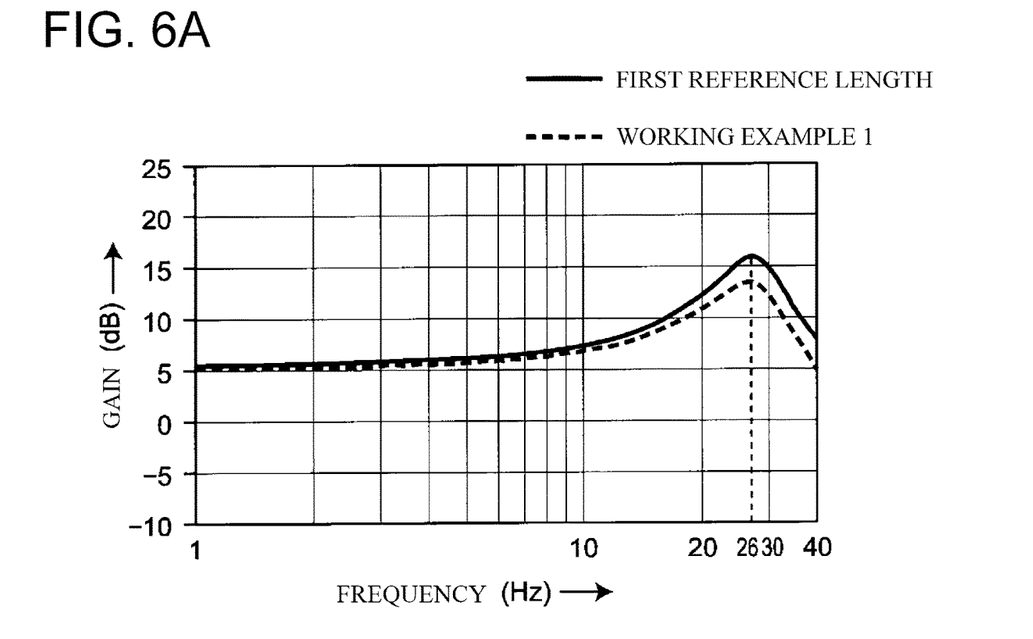
FIG. 6A is a graph relating to a fluid transfer characteristic, indicating a change in gain with respect to the frequency of the tube 22br shown in FIG. 1, when the capacity of the air tank 50br shown in FIG. 1 is set to 11.3 cc.
Figure 6B:
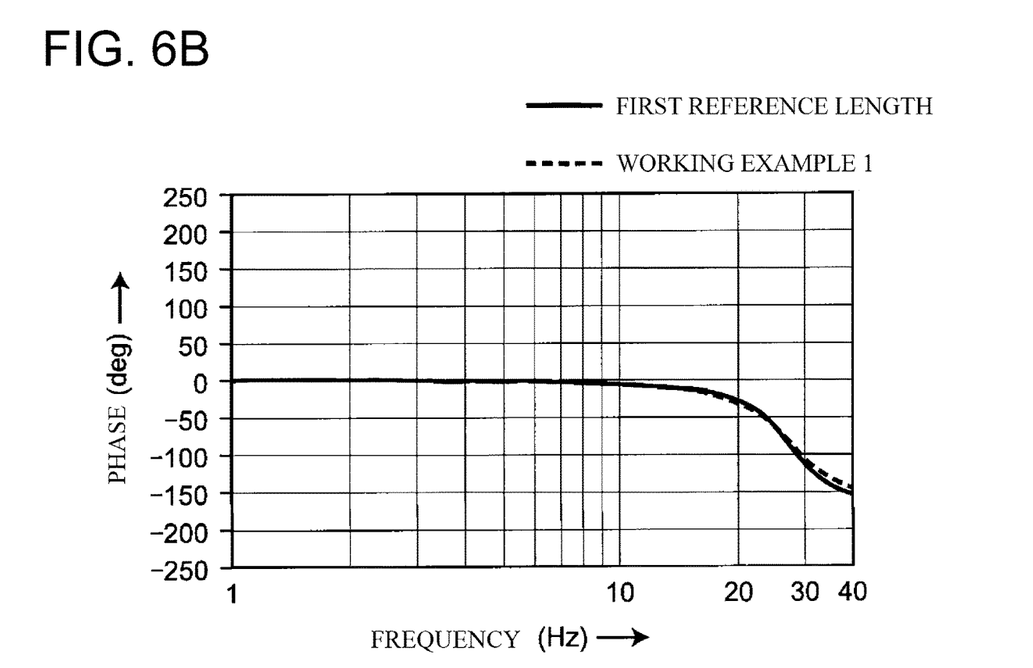
FIG. 6B is a graph relating to a fluid transfer characteristic, indicating a change in phase with respect to the frequency of the tube 22br shown in FIG. 1, when the capacity of the air tank 50br shown in FIG. 1 is set to 11.3 cc.

FIG. 6A is a graph relating to a fluid transfer characteristic, indicating a change in gain with respect to the frequency of the tube 22br shown in FIG. 1, when the capacity of the air tank 50br shown in FIG. 1 is set to 11.3 cc, and FIG. 6B is a graph relating to a fluid transfer characteristic, indicating a change in phase with respect to the frequency of the tube 22br shown in FIG. 1, when the capacity of the air tank 50br shown in FIG. 1 is set to 11.3 cc. In FIGS. 6A and 6B, the fluid transfer characteristic of the tube 22br when the length of the tube 22br is set to 2 meters (reference length) is indicated by a solid line, and the fluid transfer characteristic of the tube 22br when the length of the tube 22br is set to 1.1 meters (reference length) is indicated by a dotted line. As shown in FIG. 6A, it is understood that no shifting has occurred in the peak of the gain that occurs when the frequency is 26 (Hz). Also, as shown in FIG. 6B, it is understood that the curve indicating the change in the phase when the length of the tube 22br is set to 2 meters (reference length) and the curve indicating the change in the phase when the length of tube 22br is set to 1.1 meters approximately match. That is, the air tank 50br functions as a delay element such that the fluid transfer characteristic of the tube 22br connecting the main unit 101 and the cuff 24br matches the fluid transfer characteristic of a tube having the reference length. Accordingly, it can be understood that no error occurs in the data measured using the tube 22br with the changed length, even if the ABI and PWV are measured using a measurement algorithm defined for a tube with the reference length.

Note that the same applies to the tubes 22bl, 22ar, and 22al as well.

As described above, the air tanks 50ar and 50al are respectively provided as delay elements at predetermined positions in the lengthwise directions of the tubes 22ar and 22al such that the fluid transfer characteristics of the tubes 22ar and 22al connecting the ankle unit 102 and the cuffs 24ar and 24al match the fluid transfer characteristic of a tube with the reference length. Also, the air tanks 50br and 50bl are respectively provided as delay elements at specific positions in the lengthwise directions of the tubes 22br and 22bl such that the fluid transmission characteristics of the tubes 22br and 22bl connecting the main unit 101 and the cuffs 24br and 24bl match the fluid transfer characteristic of a tube with the reference length.

Next, the contraction length ΔL of the tubes 22ar and 22al is 15 (centimeters) (=50 (centimeters)−35 (centimeters)). Accordingly, with reference to FIG. 5, the capacities of the air tanks 50ar and 50al are each set to 1.9 (cc). The effect of this is similar to the effect of the air tank 50ar described above. Note that in the present embodiment, the capacities of the air tanks 50ar and 50al are very small, and therefore can also be omitted.

Modified Example

Figure 7:
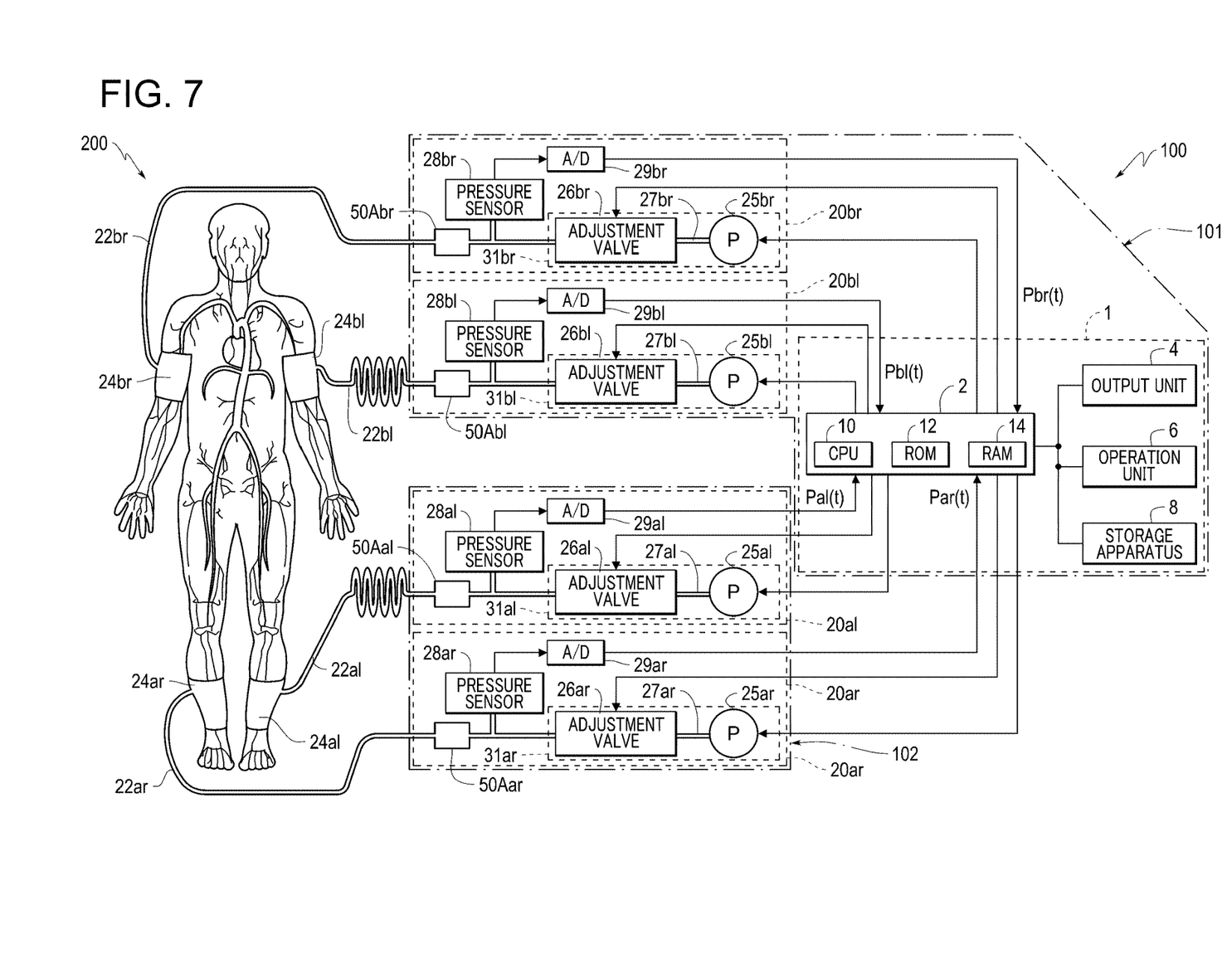
FIG. 7 is a block diagram schematically showing a configuration of a control system inside of a blood pressure pulse wave measurement apparatus 100A according to a modified example of the embodiment of the present invention.

FIG. 7 is a block diagram schematically showing a configuration of a control system inside of a blood pressure pulse wave measurement apparatus 100A of the present invention. The blood pressure pulse wave measurement apparatus 100A according to the present modified example differs from the blood pressure pulse wave measurement apparatus 100 shown in FIG. 2 in that it includes air tanks 50Abr and 50Abl provided on the end portions of the tubes 22br and 22bl in the main unit 101, and air tanks 50Aar and 50Aal included on the end portions of the tubes 22ar and 22al in the ankle unit 102, instead of the air tanks 50ar, 50al, 50br, and 50bl and the tubes 51ar, 51al, 51br, and 51bl.

With the blood pressure pulse wave measurement apparatus 100A according to the modified example above, operations and effects similar to those of the above-described embodiment can be obtained. Furthermore, compared to the above-described embodiment, the air tanks are provided inside of the main unit 101 or the ankle unit 102, and therefore do not become hindrances when the measurement subject attaches the upper arm and ankle cuffs to the upper arms and ankles of the measurement subject.

Note that in the above-described embodiment, the control unit 2 may calculate an index such as the CAVI (Cardio Ankle Vascular Index) based on the heart-ankle pulse wave velocity haPWV. Also, in the above-described embodiment described an example in which the cuffs 24ar, 24al, 24br, and 24bl are attached only to the right ankle, left ankle, right upper arm, and left upper arm. However, there is no limitation to this. The measurement part to which the cuffs 24ar, 24al, 24br, and 24bl are to be attached may be a wrist, a fingertip, or the like.

The above-described embodiments are exemplary, and various modifications are possible without departing from the scope of the invention. The above-described multiple embodiments can be achieved independently, and the embodiments can also be combined. Also, the various features of the different embodiments can also be achieved independently, and the features of the different embodiments can also be combined.

REFERENCE SIGNS LIST

1 Information processing unit
2 Control unit
4 Output unit
6 Operation unit
8 Storage apparatus
10 CPU
12 ROM
14 RAM
20ar, 20al, 20br, 20bl Detection unit
22ar, 22al, 22br, 22bl, 27ar, 27al, 27br, 27bl, 51ar, 51al, 51br, 51bl Tube
23 Connection cable
24ar, 24al, 24br, 24bl Cuff
25ar, 25al, 25br, 25bl Pressure pump
26ar, 26al, 26br, 26bl Adjustment valve
28ar, 28al, 28br, 28bl Pressure sensor
29ar, 29al, 29br, 29bl A/D conversion unit
40 Display screen
50ar, 50al, 50br, 50bl, 50Aar, 50Aal, 50Abr, 50Abl Air tank
60 Operation switch
100, 100A Blood pressure pulse wave measurement apparatus
101 Main unit
101e,101f Hook
102 Ankle unit
200 Measurement subject
300 Storage wagon
301 Leg
302 Support column
303 Placement platform
304 Storage box

The invention claimed is:

1. A blood pressure pulse wave measurement apparatus for measuring an ankle brachial index and a pulse wave velocity, comprising:
a first cuff for pressing an upper limb of a measurement subject;
a second cuff for pressing a lower limb of the measurement subject;
a first tube having a first predetermined length and including a first end and a second end, the first end of the first tube extending from the first cuff;
a second tube having a second predetermined length and including a first end and a second end, the first end of the second tube extending from the second cuff;
a first sensor that is connected to the second end of the first tube to transmit a first pulse wave from the first cuff through the first tube to the first sensor, the first sensor being configured to detect the transmitted first pulse wave;
a second sensor that is connected to the second end of the second tube to transmit a second pulse wave from the second cuff through the second tube to the second sensor, the second sensor being configured to detect the transmitted second pulse wave;
a controller configured to respectively calculate an ankle-brachial blood pressure ratio and a pulse wave velocity using the first and second pulse waves;
a first air tank provided at a first specific position in a lengthwise direction of the first tube via a first branch tube branching out from the first tube; and
a second air tank provided at a second specific position in the lengthwise direction of the second tube via a second branch tube branching out from the second tube, wherein:
the first air tank delays a transfer characteristic of the first tube such that the transfer characteristic of the first tube, provided between the first cuff and the first sensor, matches a transfer characteristic of a first reference tube having a predetermined first reference length, and
the second air tank delays a transfer characteristic of the second tube, provided between the second cuff and the second sensor, such that the transfer characteristic of the second tube matches a transfer characteristic of a second reference tube having a predetermined second reference length.

2. The blood pressure pulse wave measurement apparatus according to claim 1, wherein:
the first sensor is arranged in a first housing and the second sensor is arranged in a second housing,
the first air tank is provided on an end portion of the first tube in the first housing, and
the second air tank is provided on an end portion of the second tube in the second housing.

3. The blood pressure pulse wave measurement apparatus according to claim 1, wherein:
the first air tank is configured to store a first predetermined quantity of air and the second air tank is configured to store a second predetermined quantity of air.

* * * * *